(12) United States Patent
Chen et al.

(10) Patent No.: US 12,198,454 B2
(45) Date of Patent: Jan. 14, 2025

(54) ATTENTION MECHANISM-BASED 12-LEAD ELECTROCARDIOGRAM CLASSIFICATION METHOD AND APPARATUS

(71) Applicant: BOE TECHNOLOGY GROUP CO., LTD., Beijing (CN)

(72) Inventors: Xue Chen, Beijing (CN); Jinny Liu, Beijing (CN); Yude Li, Beijing (CN); Xianqiang Ni, Beijing (CN); Shuobin Liang, Beijing (CN); Li Zhou, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 588 days.

(21) Appl. No.: 17/513,473

(22) Filed: Oct. 28, 2021

(65) Prior Publication Data

US 2022/0309268 A1    Sep. 29, 2022

(30) Foreign Application Priority Data

Mar. 26, 2021    (CN) .......................... 202110327367.4

(51) Int. Cl.
*G06V 20/64*    (2022.01)
*A61B 5/30*    (2021.01)
(Continued)

(52) U.S. Cl.
CPC .............. *G06V 20/64* (2022.01); *A61B 5/303* (2021.01); *A61B 5/308* (2021.01);
(Continued)

(58) Field of Classification Search
CPC ...... G06V 20/64; G06V 10/147; G06V 10/42; G06V 10/95; G06V 2201/03; G06V 10/82;
(Continued)

(56) References Cited

U.S. PATENT DOCUMENTS

2023/0037958 A1* 2/2023 Liba ........................... G06T 7/50
2023/0329646 A1* 10/2023 Zhou ....................... G16H 50/30

FOREIGN PATENT DOCUMENTS

| CN | 110717415 A | 1/2020 |
| CN | 111657914 A | 9/2020 |

(Continued)

OTHER PUBLICATIONS

Zhang J, Liu A, Gao M, Chen X, Zhang X, Chen X. ECG-based multi-class arrhythmia detection using spatio-temporal attention-based convolutional recurrent neural network. Artificial Intelligence in Medicine. Jun. 1, 2020;106:101856. (Year: 2020).*

(Continued)

*Primary Examiner* — Fayyaz Alam
(74) *Attorney, Agent, or Firm* — Myers Bigel, P.A.

(57) ABSTRACT

An attention mechanism-based 12-lead electrocardiogram (ECG) classification method is described, the method including acquiring an original image of a 12-lead ECG, segmenting waveform data recorded in the original image to obtain segmented waveform data for each lead in the 12-lead ECG, performing depth feature extraction on the segmented waveform data of said each lead to obtain a first feature map of said each lead, performing feature transformation on the first feature map of said each lead based on an attention mechanism to obtain a depth feature of said each lead, and classifying the depth feature of said each lead to obtain a classification result for the original image. The classification method can make full use of the 12-lead ECG for overall classification and improve the accuracy of image classification.

18 Claims, 4 Drawing Sheets

(51) Int. Cl.
| | |
|---|---|
| *A61B 5/308* | (2021.01) |
| *G06F 18/2137* | (2023.01) |
| *G06F 18/214* | (2023.01) |
| *G06F 18/241* | (2023.01) |
| *G06V 10/147* | (2022.01) |
| *G06V 10/42* | (2022.01) |
| *G06V 10/94* | (2022.01) |
| *G16H 10/60* | (2018.01) |
| *G16H 50/20* | (2018.01) |

(52) U.S. Cl.
CPC ...... *G06F 18/2137* (2023.01); *G06F 18/2148* (2023.01); *G06F 18/241* (2023.01); *G06V 10/147* (2022.01); *G06V 10/42* (2022.01); *G06V 10/95* (2022.01); *G16H 10/60* (2018.01); *G16H 50/20* (2018.01); *A61B 2560/0223* (2013.01); *A61B 2562/222* (2013.01); *G06V 2201/03* (2022.01)

(58) Field of Classification Search
CPC . A61B 5/303; A61B 5/308; A61B 2560/0223; A61B 2562/222; A61B 5/7264; G06F 18/2137; G06F 18/2148; G06F 18/241; G06F 2218/00; G16H 10/60; G16H 50/20; G16H 30/40
See application file for complete search history.

(56) References Cited

FOREIGN PATENT DOCUMENTS

| CN | 111657926 A | 9/2020 |
|---|---|---|
| CN | 111743531 A | 10/2020 |
| CN | 111783961 A | 10/2020 |

OTHER PUBLICATIONS

Wang J, Qiao X, Liu C, Wang X, Liu Y, Yao L, Zhang H. Automated ECG classification using a non-local convolutional block attention module. Computer Methods and Programs in Biomedicine. May 1, 2021;203:106006. (Year: 2021).*

Fu L, Lu B, Nie B, Peng Z, Liu H, Pi X. Hybrid network with attention mechanism for detection and location of myocardial infarction based on 12-lead electrocardiogram signals. Sensors. Feb. 14, 2020;20(4):1020. (Year: 2020).*

Natarajan A, Chang Y, Mariani S, Rahman A, Boverman G, Vij S, Rubin J. A wide and deep transformer neural network for 12-lead ECG classification. In2020 Computing in Cardiology Sep. 13, 2020 (pp. 1-4). IEEE. (Year: 2020).*

Tung H, Zheng C, Mao X, Qian D. Multi-Lead ECG Classification via an Information-Based Attention Convolutional Neural Network. arXiv preprint arXiv:2003.12009. Mar. 25, 2020. (Year: 2020) .*

Zhen-xing Wang, et al., "Shape recognition algorithm for ST-segment of ECG signal", Journal of Computer Applications, vol. 31, No. 10, Oct. 2011, 4 pp.

Second Office Action for CN application No. 202110327367.4 with translation mailed May 18, 2023, 18 pages.

"Intensive reading of deep learning papers (5): SENet", downloaded from https://blog.csdn.net/hwl19951007/article/details/84961735, Dec. 27, 2020, 10 pp.

D. Wang, et al., "Automatic Detection of Arrhythmia Based on Multi-Resolution Representation of ECG Signal", Sensors 2020, vol. 20, No. 6, 1579; doi:10.3390/s20061579, 12 pp.

J. Chen et al., "SE-ECGNet: Multi-scale SE-Net for Multi-lead ECG Data," IEEE 2020 Computing in Cardiology, 2020, doi: 10.22489/CinC.2020.085, 4 pp.

J. Faganeli, et al., "Automatic Distinguishing Between Ischemic and Heart-Rate Related Transient ST Segment Episodes in Ambulatory ECG Records", Computers in Cardiology, vol. 35, 2008, pp. 381-384.

J. Hu et al., "Squeeze-and-Excitation Networks", downloaded from http://image-net.org/challenges/LSVRC/2017/results, May 16, 2019, 13 pp.

L. Fu et al., "Hybrid Network with Attention Mechanism for Detection and Location of Myocardial Infarction Based on 12-Lead Electrocardiogram Signals", Sensors 2020, vol. 20(4), 1020; doi:10.3390/s20041020, 24 pp.

Li-Yan Wang, et al., "Scheduling Jobs With General Learning Functions", J Syst Sci Syst Eng, vol. 20, No. 1, Mar. 2011, pp. 119-125.

P de Chazal, "Different Techniques used to Improve the Performance of a Classifier of the Twelve-Lead Electrocardiogram", Computers in Cardiology, vol. 28, 2001, pp. 525-528.

Philip de Chazal, et al., "Automatic Classification of Heartbeats Using ECG Morphology and Heartbeat Interval Features ", IEEE Transactions on Biomedical Engineering, vol. 51, No. 7, Jul. 2004, pp. 1196-1206.

Ran Xiao, et al., "A Deep Learning Approach to Examine Ischemic ST Changes in Ambulatory ECG Recordings", AMIA Jt Summits Transl Sci Proc., 2018, pp. 256-262.

W. Cai, et al., "Automatic 12-lead ECG Classification Using Deep Neural Networks," IEEE 2020 Computing in Cardiology, 2020, doi: 10.22489/CinC.2020.039, 4 pp.

Yan Yan et al., "A Restricted Boltzmann Machine Based Two-lead Electrocardiography Classification", 2015 IEEE 12th International Conference on Wearable and Implantable Body Sensor Networks (BSN), 2015, 9 pp.

Zhao Shen, et al., "An Algorithm of ST Segment Classification and Detection", 2010 IEEE International Conference on Automation and Logistics, 2010, pp. 559-564.

* cited by examiner

ATTENTION MECHANISM-BASED 12-LEAD ELECTROCARDIOGRAM CLASSIFICATION METHOD AND APPARATUS

RELATED APPLICATION

The present application claims the priority of Chinese Patent Application No. 202110327367.4 filed on Mar. 26, 2021, the entire disclosure of which is incorporated herein by reference.

FIELD

The present disclosure relates to the field of image processing, specifically to medical image processing, especially to an attention mechanism-based 12-lead electrocardiogram (ECG) classification method and apparatus.

BACKGROUND

With the development of depth learning technologies, significant results have also been achieved in the analysis of ECG signals. However, in the related arts, detection and analysis are usually performed using a single-lead electrocardiogram only, so that the condition of the heart cannot be well expressed because the heart has a three-dimensional structure, seriously influencing the effect of image analysis.

SUMMARY

In view of the above-mentioned shortcomings or deficiencies in the prior art, it is desirable to provide an attention mechanism-based 12-lead electrocardiogram (ECG) classification method and apparatus, which can make full use of the 12-lead ECG for overall classification and improve the accuracy of image classification.

According to a first aspect of the present disclosure, there is provided an attention mechanism-based 12-lead electrocardiogram (ECG) classification method, comprising:
  acquiring an original image of a 12-lead ECG;
  segmenting waveform data recorded in the original image to obtain segmented waveform data for each lead in the 12-lead ECG;
  performing depth feature extraction on the segmented waveform data of said each lead to obtain a first feature map of said each lead;
  performing feature transformation on the first feature map of said each lead based on an attention mechanism to obtain a depth feature of said each lead;
  classifying the depth feature of said each lead to obtain a classification result for the original image.

In some embodiments, said segmenting waveform data recorded in the original image to obtain segmented waveform data for said each lead in the 12-lead ECG comprises:
  for said each lead image, identifying a position of each target feature in the lead image;
  for said each target feature, taking the position of the target feature as a center, and segmenting the waveform data based on a preset sliding window width to obtain segmented waveform data of each lead.

In some embodiments, said performing feature transformation on the first feature map of said each lead based on an attention mechanism to obtain a depth feature of said each lead comprises:
  performing at least one convolution operation processing on the first feature map to obtain a second feature map;
  performing a first activation operation on the second feature map to obtain embedded information;
  performing a second activation operation on the embedded information to obtain a feature weight corresponding to said each lead;
  obtaining the depth feature of said each lead based on the feature weight and the first feature map.

In some embodiments, the first activation operation is performed on the second feature map using the following formula:

$$p(F[c][j]) = \frac{e^{F[c][j]}}{\sum_{j=0}^{W \times H - 1} e^{F[c][j]}}$$

wherein p represents an activation function, and F[c][j] represents a value of a j-th element in the second feature map of a c-th lead.

In some embodiments, the second activation operation is performed on the embedded information using the following formula:

$$N(z) = -\sum_{j=0}^{W \times H - 1} p(F[c][j]) \log p(F[c][j])$$

wherein z represents a random variable of a c-th lead, and N represents a feature weight to which the c-th lead corresponds.

In some embodiments, said obtaining the depth feature of said each lead based on the feature weight and the first feature map comprises:
  continuously inputting the feature weight of each lead into two fully connected layers to obtain an attention weight corresponding to each lead;
  obtaining the depth feature of said each lead based on the attention weight corresponding to said each lead and the first feature map.

In some embodiments, said continuously inputting the feature weight of each lead into two fully connected layers to obtain an attention weight corresponding to each lead comprises:
  compressing a dimension of the feature weight of each lead using a first fully connected layer of the two fully connected layers to determine a dependency relationship between leads;
  calibrating the feature weight of each lead using the dependency relationship to obtain an attention weight corresponding to said each lead.

In some embodiments, said obtaining the depth feature of each lead based on the attention weight corresponding to each lead and the first feature map comprises:
  multiplying the first feature map of each lead by the attention weight corresponding to each lead to obtain the depth feature of each lead.

In some embodiments, said performing depth feature extraction on the segmented waveform data of said each lead to obtain a first feature map of said each lead comprises:
  inputting the segmented waveform data of said each lead into a trained neural network model to obtain the first feature map is corresponding to each lead, the first feature map corresponding to said each lead being identical in size.

According to a second aspect of the present disclosure, there is provided an attention mechanism-based 12-lead ECG classification apparatus, comprising:

an acquirer configured to acquire an original image of a 12-lead ECG;

a segmenter configured to segment waveform data recorded in the original image to obtain segmented waveform data for each lead in the 12-lead ECG;

a feature extractor configured to perform depth feature extraction on the segmented waveform data of said each lead to obtain a first feature map of said each lead;

a feature transformer configured to perform feature transformation on the first feature map of said each lead based on the attention mechanism to obtain a depth feature of said each lead;

a classifier configured to classify the depth feature of said each lead to obtain a classification result for the original image.

According to a third aspect of the present disclosure, there is provided an electronic device comprising a memory and a processor, the memory storing computer instructions executable on the processor, wherein any method described in the first aspect of the present disclosure is implemented when the computer instructions are executed by the processor.

According to a fourth aspect of the present disclosure, there is provided a non-transitory computer-readable storage medium having computer instructions stored thereon, wherein any method described in the first aspect of the present disclosure is implemented when the computer instructions are executed by a processor.

The additional aspects and advantages of the present invention will be partially given in the following description, and part of them will become apparent from the following description, or be appreciated by practicing the present invention.

BRIEF DESCRIPTION OF THE DRAWINGS

By reading the detailed description of the non-limiting embodiments with reference to the following drawings, other features, purposes and advantages of the present disclosure will become more apparent.

DETAILED DESCRIPTION

Figure 1:
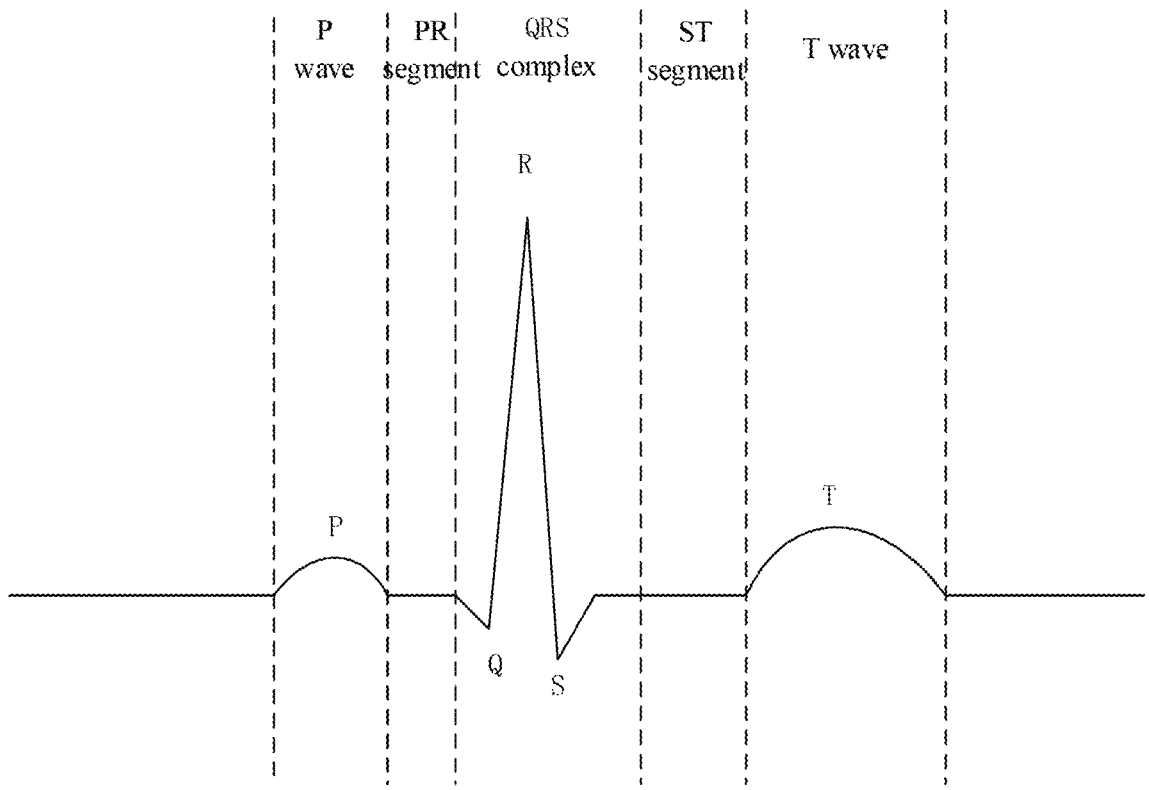
FIG. 1 is a schematic view of an ECG waveform according to an embodiment of the present disclosure.

The present disclosure will be further described in detail below with reference to the accompanying drawings and embodiments. It can be understood that the specific embodiments described here are only used to explain related solutions, but not to limit the related solutions. In addition, it is to be further noted that, to facilitate description, only the parts related to the invention are shown in the drawings.

It is to be noted that the embodiments in the present disclosure and the features in the embodiments can be combined with each other in the case of causing no conflict. Hereinafter, the present disclosure will be described in detail with reference to the drawings and in conjunction with the embodiments.

An ECG signal is a function of the ECG voltage amplitude measured by a body surface electrode varying over time, and belongs to a time-domain waveform signal. Although the ECG waveforms measured from different leads on different parts of the human body surface (the position where an electrode is placed on the human body surface and the connection between the electrode and the amplifier when recording an ECG are called a lead of the ECG) are different from each other, and the ECG signals of different individuals are distinct, all normal ECG waveform cycles can be mainly divided into P wave, PR segment, QRS complex, ST segment, T wave, etc., and each feature sub-band represents a certain physiological significance.

The ECG waveform is now taken as an example. As shown in FIG. 1, main components of the ECG waveform and characteristics thereof are briefly introduced.

(1) P wave: It is also called an atrial depolarization wave and reflects potential changes during the depolarization process of the left and right atria. The waveform is generally round, blunt and smooth, lasting 0.08-0.11 s. The amplitude does not exceed 0.5 mV. The potential change generated by the repolarization of two atria is called Ta wave. It usually overlaps the PR segment, the QRS complex or the ST segment, and has low amplitude, which is not easy to identify on the ECG.

(2) PR segment: It is a time interval between the start point of the P wave and the start point of the QRS complex, and reflects a period of time from the beginning of atrial depolarization to the beginning of ventricular depolarization. The PR interval for normal adults is 0.12-0.2 s. In the case of more than 0.205 s, it generally indicates the occurrence of atrioventricular block. The length of the P→R segment is related to the age and the heart rate.

(3) QRS complex: It reflects potential changes during the depolarization process of two ventricles. A typical QRS complex includes three closely connected potential fluctuations. The first downward wave is called a Q wave, followed by an upward high and sharp R wave, and the last wave is a downward S wave. These three waves may not all appear in different leads, and the amplitude of each wave also varies greatly. It lasts about 0.06-0.105 s.

(4) ST segment: It refers to a line segment between the end point of the QRS complex and the start point of the T wave. Normally, the ST segment should be on the equipotential line. During this period of time, all parts of the ventricles have entered a state of depolarization, but have not yet begun to repolarize, so there is no potential difference between the parts of the ventricles, and the ECG curve returns to the baseline level. However, if coronary ischemia or myocardial infarction occurs, the ST segment will deviate from the baseline (i.e. offset) and exceed a certain amplitude range.

(5) T wave: It represents repolarization of the ventricles, the waveform is round and blunt, and the ascending and descending branches are not completely symmetrical. The anterior branch of the is waveform is longer and the posterior branch of the waveform is shorter, occupying about 0.05-0.255 s. The direction of the T wave should be consistent with the main wave direction of the QRS complex. In a lead dominated by R wave, its amplitude should not be less than 1/10 of the R wave of this lead.

(6) Q→T interval: It refers to the time from the start point of the QRS complex to the end point of the T wave, and represents the time required from the start of depolarization of the ventricles to the completion of all repolarization. The length of this interval is closely related to the heart rate. The faster the heart rate is, the shorter the Q→T interval will be, and on the contrary, the slower the heart rate is, the longer the Q→T interval will be. The normal Q→T interval varies with the heart rate, age and gender. When the heart rate is 75 beats/min, the Q→T interval is 0.30-0.405 s.

On this basis, it can be obtained that myocardial ischemia can be analyzed according to changes in the ST segment in the ECG to make a diagnosis. Myocardial ischemia will cause myocardial infarction in severe cases. If patients suffering from myocardial infarction can be diagnosed in time and applied with effective treatment, the myocardium will not be damaged after recovery and there will be no sequelae. Therefore, timely screening of myocardial ischemia is of great significance for clinical heart diseases.

A variety of methods for classification and identification of ECG images have been proposed in the related arts. For example, there is proposed a method for ST segment classification using polynomial fitting and template matching methods. The keys to this method lie in accurate positioning of feature locations, establishment of templates, and accurate template matching. This method can achieve a better classification effect, but the process thereof is complicated. The template is difficult to establish, the template matching has low accuracy, and each process implemented may involve a certain error, is which greatly affects the classification effect. For another example, there is proposed a method of identifying the ST segment based on a least squares algorithm. Firstly, the detected QRS complex is found using wavelets, the key feature points of the ECG signal waveform (including feature points such as start points and end points of the QRS complex and the T wave) are detected, the offset direction of the ST segment is then determined according to the feature points, and finally the morphological type of the ST segment is determined by a polynomial fitting algorithm based on the slope and the concave-convex direction of the ST segment. The disadvantages of this method are that it is more sensitive to noise, and there is a certain error in the feature point positioning. For another example, there is proposed a method of dividing the ST segment detection into two parts. Firstly, the offset direction of the ST segment is calculated using wavelet transform and morphological methods. The wavelet transform is used to extract the features of the ST segment, and the ST segment is classified according to these features. The change trend of ST-segment waveform within 30 minutes is analyzed, and the change trend is finally applied to the detection of myocardial ischemia. This classification method is simple, but it is complicated to process the feature point identification.

On this basis, the present disclosure proposes an attention mechanism-based 12-lead ECG classification method and apparatus. It is to be pointed out that the 12-lead ECG refers to conventional 12 leads in the ECG examination, including three limb leads, namely lead I, lead II and lead III, three augmented limb leads, namely lead AVR, lead AVL and lead AVF, and six chest leads, namely leads V1, V2, V3, V4, V5 and V6.

The attention mechanism-based 12-lead ECG classification method and apparatus proposed by embodiments of the present disclosure will be described below with reference to the is accompanying drawings.

Figure 2:
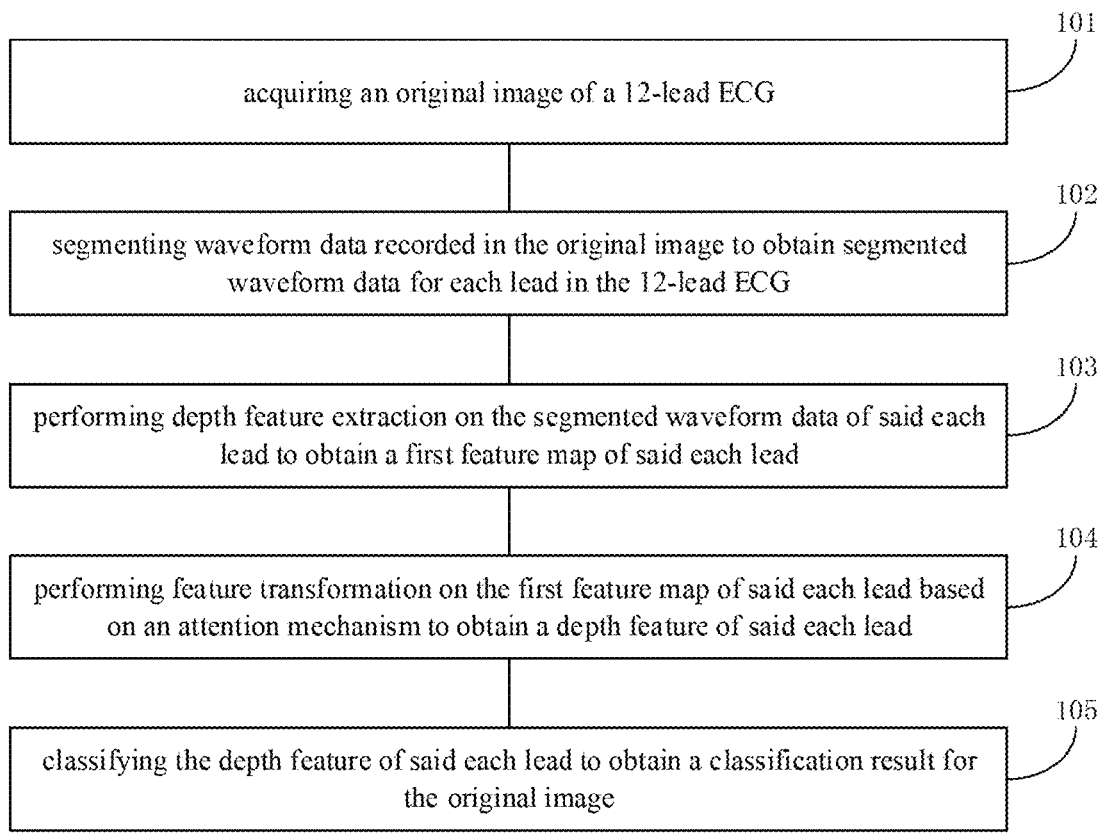
FIG. 2 is a flow chart of an attention mechanism-based 12-lead ECG classification method according to an embodiment of the present disclosure.

FIG. 2 is a flow chart of an attention mechanism-based 12-lead ECG classification method proposed by an embodiment of the disclosure. It is to be noted that the subject that executes the attention mechanism-based 12-lead ECG classification method of this embodiment is an attention mechanism-based 12-lead ECG classification apparatus. The attention mechanism-based 12-lead ECG classification apparatus may be configured in an electronic device, or in a server for controlling the electronic device, and the server may communicate with the electronic device to control it.

The electronic device in this embodiment may include, but is not limited to, a personal computer, a desktop computer, a smart phone, a smart speaker, etc., which is not specifically defined in this embodiment.

Figure 3:
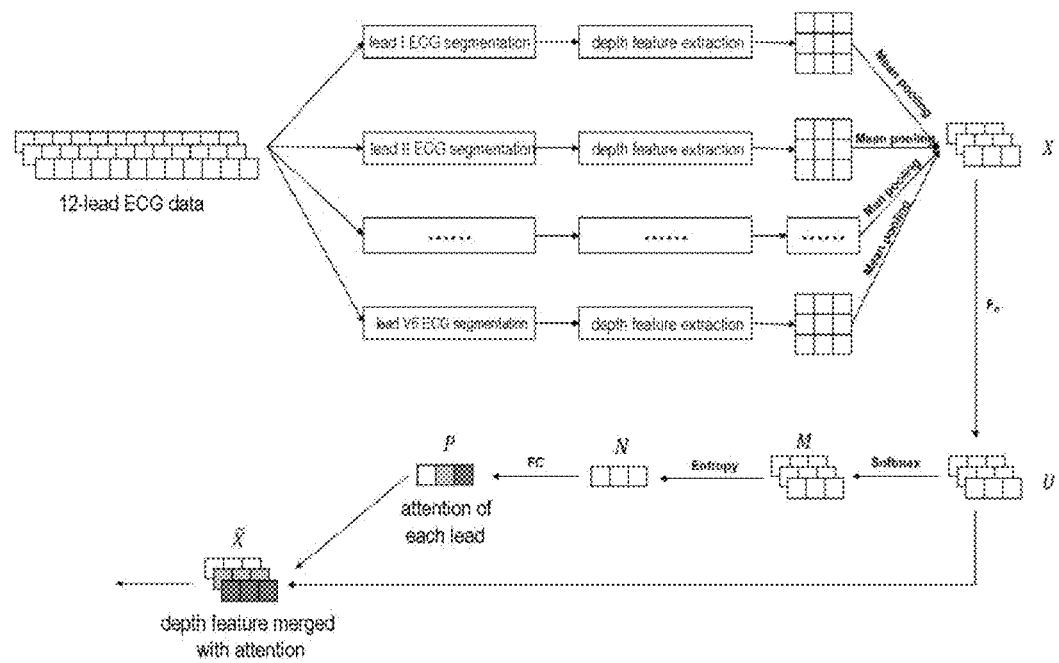
FIG. 3 is a schematic view illustrating the principle of an attention mechanism-based 12-lead ECG classification method according to an embodiment of the present disclosure.

The attention mechanism-based 12-lead ECG classification method will be described below in conjunction with FIGS. 2 and 3. The method comprises the following steps 101-105.

In step 101, an original image of a 12-lead ECG is acquired.

It is to be noted that an electrocardiogram (ECG) is an image of the electrical activity of the heart over a period of time recorded by electrodes placed on the skin. A standard ECG is a 12-lead ECG. The 12-lead ECG has two primary characteristics. The first characteristic is "integrity". Specifically, the 12-lead ECG signal records the potential of the heart at different spatial angles, which fully reflects the condition of the heart. Therefore, the 12-lead can be seen as a whole. The second characteristic is "diversity". Different leads correspond to different anatomical regions of the heart and provide different perspectives. Therefore, each lead has its unique information.

In some embodiments, the original electrocardiogram data may be down-sampled to obtain the original image of the 12-lead ECG. The sampling frequency of the processed original image may be 250 Hz, that is, ECG=Xn, $1 \leq n \leq L$, where L is the signal length.

In step 102, the waveform data recorded in the original image is segmented to obtain segmented waveform data for each lead in the 12-lead ECG.

In some embodiments, the waveform data recorded in the original image may be segmented in the following manner: for each lead image in the original image, identifying a position of each target feature in saidn each lead image; for said each target feature, taking the position of said each target feature as a center, and segmenting the waveform data recorded in the original image based on a preset sliding window width to obtain segmented waveform data of said each lead.

Figure 4:
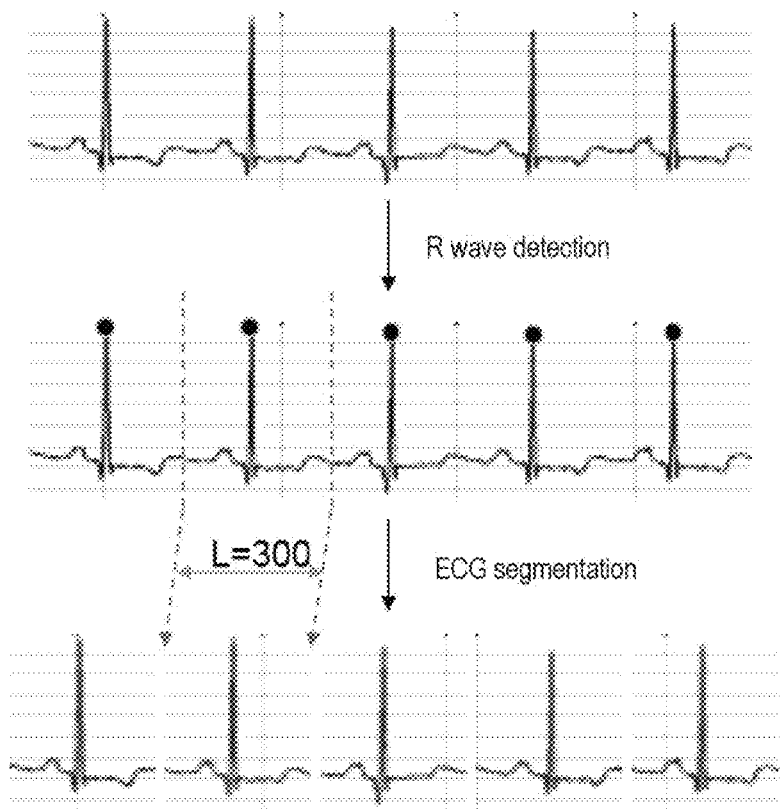
FIG. 4 is a schematic view illustrating the principle of segmenting waveform data according to an embodiment of the present disclosure.

In an embodiment of the present disclosure, the preset sliding window width may be 300, and the target feature is the R wave. That is to say, as shown in FIG. 4, the R wave in the lead image is to be identified. If the position of the i-th R wave is $X_{Ri}$, then an intercepted fragment is $[X_{Ri}-149$, $X_{Ri}+150$]. For the first R wave and the last R wave, the absent part in the fragment may be filled with 0.

In step 103, depth feature extraction is performed on the segmented waveform data of said each lead to obtain a first feature map of said each lead. As an example, depth feature extraction may be performed on the segmented waveform data based on a trained neural network to obtain a first feature map of each lead.

In an embodiment of the present disclosure, depth feature extraction is performed on the segmented waveform data using a neural network model. The optional neural network models may include but are not limited to: FCNN, CNN, RNN, CRNN, ResNet, RCR-net, etc. For example, the ResNet14 model may be used in the embodiment of the present disclosure. Specifically, the segmented waveform data may be input to the trained ResNet14 model to obtain the first feature map corresponding to each lead, and the first feature map corresponding to each lead is identical in size.

Figure 5:
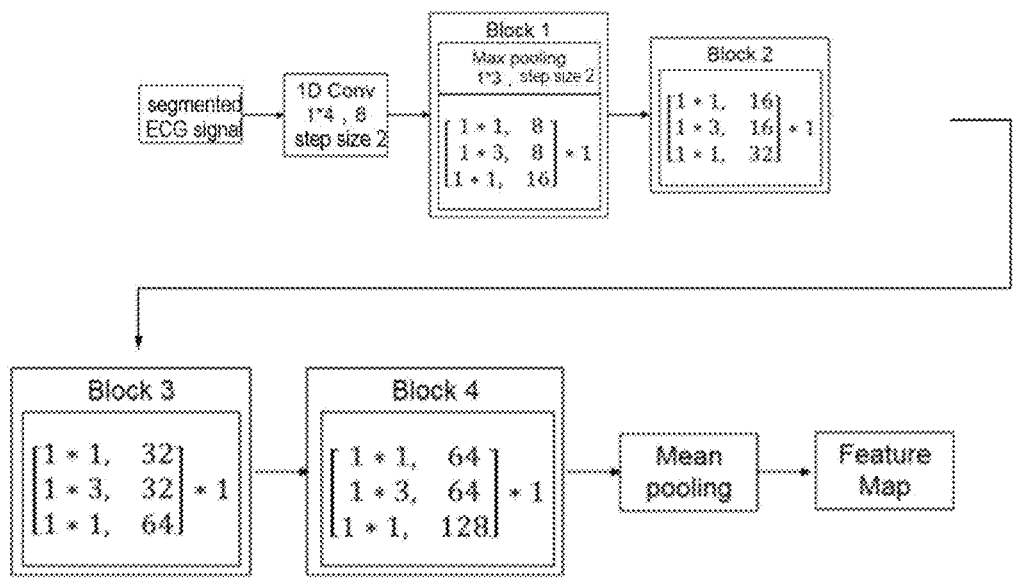
FIG. 5 is a schematic structural view of a ResNet14 model according to an embodiment of the present disclosure.

The structure of the ResNet14 model is shown in FIG. 5. In the ResNet14 model, the convolutional layer includes a one-dimensional sub-convolution layer 1D_Conv, a first convolution block Block1, a second convolution block Block2, a third convolution block Block3, a fourth convolution block Block4, and a fully connected layer FC, which involves 14 layers of convolution in total. The 14 layers of convolution all have a step size of 2. The first convolution block Block1 includes a first sub-convolution layer, a second sub-convolution layer, and a third sub-convolution layer. The second convolution block Block2 includes a fourth sub-convolution layer, a fifth sub-convolution layer, and a sixth sub-convolution layer. The third convolution block Block3 includes a seventh sub-convolution layer, an eighth sub-convolution layer, and a ninth sub-convolution layer. The fourth convolution block Block4 includes a tenth sub-convolution layer, an eleventh sub-convolution layer, and a twelfth sub-convolution layer.

The convolution kernel of the one-dimensional sub-convolution layer 1D_Conv is 1*4, including 8 convolution channels. The convolution kernel of the first sub-convolution layer is 1*1, including 8 convolution channels. The convolution kernel of the second sub-convolution layer is 1*3, including 8 convolution channels. The convolution kernel of the third sub-convolution layer is 1*1, including 16 convolution channels. The convolution kernel of the fourth sub-convolution layer is 1*1, including 16 convolution channels. The convolution kernel of the fifth sub-convolution layer is 1*3, including convolution channels. The convolution kernel of the sixth sub-convolution layer is 1*1, including 32 convolution channels. The convolution kernel of the seventh sub-convolution layer is 1*1, including 32 convolution channels. The convolution kernel of the is eighth sub-convolution layer is 1*3, including 32 convolution channels. The convolution kernel of the ninth sub-convolution layer is 1*1, including 64 convolution channels. The convolution kernel of the tenth sub-convolution layer is 1*1, including 64 convolution channels. The convolution kernel of the eleventh sub-convolution layer is 1*3, including 64 convolution channels. The convolution kernel of the twelfth sub-convolution layer is 1*1, including 128 convolution channels. The convolution kernel of the maximum pooling layer MaxPooling is 1*3, and the step size is 2. The convolution kernel of the mean pooling layer MeanPooling is 1*3, and the step size is 2.

It should be understood that in the embodiment of the present disclosure, a mean pooling layer is added at the end of the ResNet14 model to make the size of the first feature map X of each lead identical.

In step 104, feature transformation is performed on the first feature map of each lead based on an attention mechanism to obtain a depth feature of each lead.

It is to be noted that the attention mechanism can give a higher degree of attention to the leads prone to ST segment abnormalities. The attention mechanism is implemented by an information-based squeeze and excitation block (ISE-block).

Figure 6:
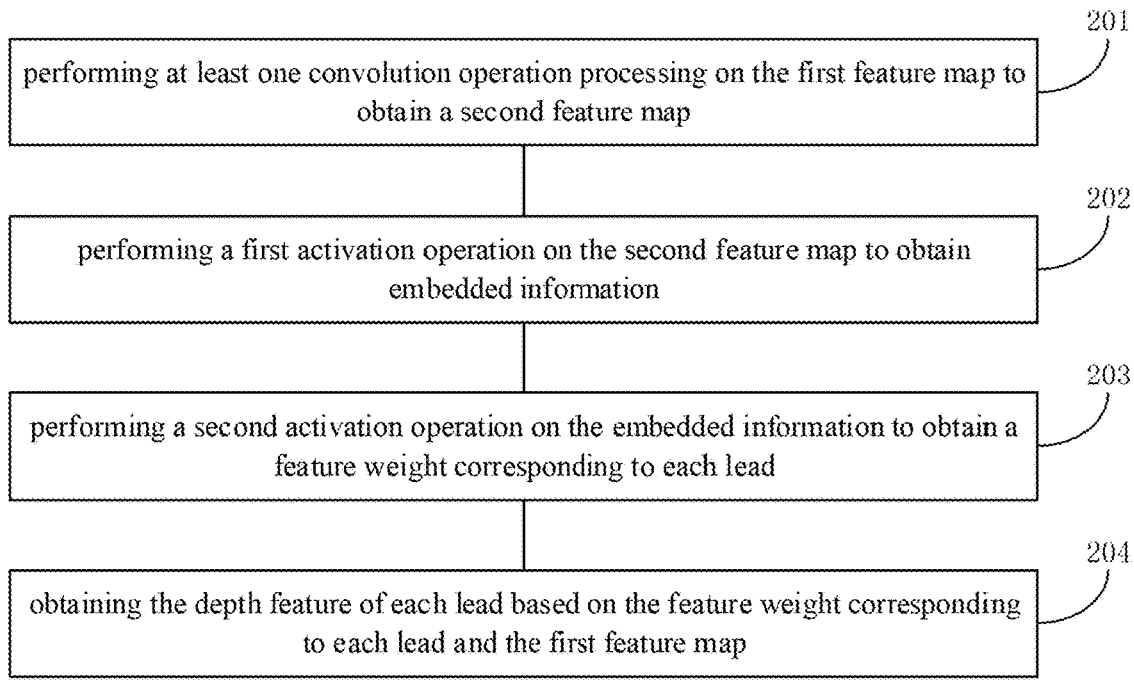
FIG. 6 is a flow chart of another attention mechanism-based 12-lead ECG classification method according to an embodiment of the present disclosure.

In some embodiments, as shown in FIG. 6, performing feature transformation on the first feature map based on an attention mechanism to obtain a depth feature of each lead may comprise the following steps 201-204.

In step 201, at least one convolution operation processing is performed on the first feature map to obtain a second feature map.

Optionally, a convolution operation is performed on the first feature map X to obtain a second feature map U, that is, $F_{tr}: X \rightarrow U$, $X \in R^{W \times H \times C}$, $U \in R^{W' \times H' \times C'}$, where H' is the height of the feature image corresponding to the first feature map, W' is the width of the feature image corresponding to the first feature map, and C' is the depth of the feature image corresponding to the first feature map. Correspondingly, H, W and C correspond to the height, width and depth of the feature image corresponding to the second feature map, respectively.

It should be understood that, in the embodiment of the present disclosure, one convolution is used to recalibrate the first feature map to be inputted, so as to improve the accuracy of subsequent feature processing. However, the number of convolution operations in the present disclosure is not limited.

In step 202, a first activation operation is performed on the second feature map to obtain embedded information.

In some embodiments, the first activation operation may be performed on the second feature map U using the following formula to obtain embedded information M, $$p(F[c][j]) = \frac{e^{F[c][j]}}{\sum_{j=0}^{W \times H - 1} e^{F[c][j]}}$$

wherein p represents an activation function, such as a softmax function, and F[c][j] represents the value of the j-th element in the second feature map of the c-th lead, where c and j are positive integers. It should be noted that the c-th lead is one of 12 leads.

It should be understood that the process of converting the second feature map U into embedded information M can be regarded as embedding of global information. In other words, the first activation operation is performed on the second feature map U first, where the first activation operation generates embedded information M by aggregating feature mappings across spatial dimensions (H×W). The functions of this feature descriptor are to generate globally distributed embedded channel feature responses and to allow information from the global receptive domain of the network to be used by all its layers.

In step 203, a second activation operation is performed on the embedded information to obtain a feature weight corresponding to each lead.

In some embodiments, the second activation operation may be performed on the embedded information M using the following formula to obtain a feature weight N corresponding to each lead, $$N(z) = - \sum_{j=0}^{W \times H-1} p(F[c][j]) \log p(F[c][j])$$

wherein z represents a random variable of the c-th lead, and N represents the weight of the c-th lead, where c and j are positive integers.

In step 204, the depth feature of each lead is obtained based on the feature weight corresponding to each lead and the first feature map.

It is to be noted that when the depth feature is obtained based on the feature weight corresponding to each lead and the first feature map, the feature weight corresponding to each lead may be continuously input into two fully connected layers to obtain an attention weight corresponding to each lead.

Figure 7:
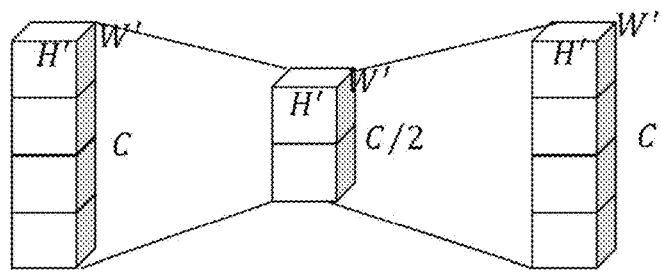
FIG. 7 is a schematic structural view of two consecutive fully connected layers according to an embodiment of the present disclosure.

It is to be noted that, in order to prevent the model from becoming complicated and taking into account generalization factors, two fully connected layers are set in the present disclosure as a bottleneck to parameterize the gate mechanism to obtain an attention weight P of each lead, as shown in FIG. 7. In the design of this structure, the initial motivation is to limit the complexity of the model and assist generalization. Introducing this structure makes full use of the information between the feature maps of each lead to learn the nonlinear relationship between leads. Firstly, the dimension of the inputted feature weight N corresponding to each lead is compressed from the C dimension to the C/2 dimension. This part can learn the dependency relationship between leads as much as possible. This dependency relationship is then used to recalibrate the lead weight, is and the C/2 dimension is restored to the C dimension to obtain a calibrated weight, that is, the attention weight P of each lead. Moreover, this process needs to meet the following conditions:

1) the correlation between leads is non-linear to fit the non-linear features;
2) the leads need to be independent of each other after they are calibrated.

The number of input nodes in the FC layer is equal to the number of output nodes therein, which is equal to the number of channels in the input feature mappings of the ISE block.

Then, the first feature map X of said each lead is multiplied with the calculated attention weight, so that a depth feature X̃ added with the attention weight can be obtained.

In step 105, the depth feature of each lead is classified to obtain a classification result for the original image. As an example, the depth feature can be classified based on the fully connected layer to obtain a classification result for the original image.

In some embodiments, the depth features may be classified using a fully connected layer and a softmax layer. Optionally, the classification result includes two types, namely normal and abnormal.

It has been verified that the method proposed by the present disclosure can achieve a sensitivity index of 0.88 and a specificity index of 0.87 for the screening of ST-segment abnormalities.

In summary, the attention mechanism-based 12-lead ECG classification method proposed by the embodiment of the present disclosure can effectively improve the accuracy of abnormality screening by, for example, performing feature extraction on the original image of the 12-lead ECG using a neural network model. Meanwhile, combined with the attention mechanism, it can give a higher degree of attention to the leads prone to ST-segment abnormalities, effectively improving the accuracy of abnormality screening.

It is to be noted that although the operations of the method of the present invention are described in a specific order in the drawings, this does not require or imply that these operations must be performed in the specific order, or that all the operations shown must be performed to achieve the desired result.

Figure 8:
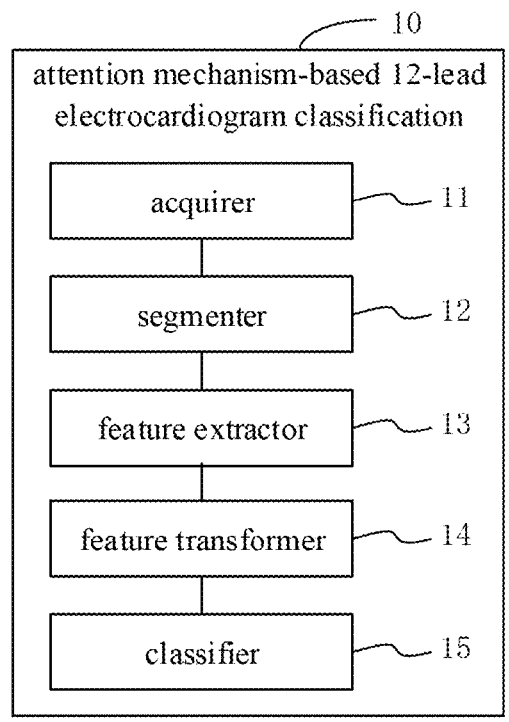
FIG. 8 is a block diagram of an attention mechanism-based 12-lead ECG classification apparatus according to an embodiment of the present disclosure.

FIG. 8 is a block diagram of an attention mechanism-based 12-lead ECG classification apparatus according to an embodiment of the present disclosure.

As shown in FIG. 8, an attention mechanism-based 12-lead ECG classification apparatus 10 proposed by an embodiment of the present disclosure comprises:

an acquirer 11 configured to acquire an original image of a 12-lead ECG;

a segmenter 12 configured to segment waveform data recorded in the original image to obtain segmented waveform data for each lead in the 12-lead ECG;

a feature extractor 13 configured to perform depth feature extraction on the segmented waveform data of said each lead to obtain a first feature map of said each lead;

a feature transformer 14 configured to perform feature transformation on the first feature map of said each lead based on the attention mechanism to obtain a depth feature of each lead;

a classifier 15 configured to classify the depth feature of said each lead to obtain a classification result for the original image.

In some embodiments, the segmenter 12 is further configured to:

for said each lead image, identify a position of each target feature in the lead image;

for said each target feature, taking the position of the target feature as the center, segment the waveform data based on a preset sliding window width to obtain segmented waveform data of each is lead.

In some embodiments, the feature transformer 14 is also configured to:

perform at least one convolution operation processing on the first feature map to obtain a second feature map;

perform a first activation operation on the second feature map to obtain embedded information;

perform a second activation operation on the embedded information to obtain a feature weight corresponding to each lead;

obtain the depth feature of each lead based on the feature weight and the first feature map.

In some embodiments, the feature transformer 14 is further configured to perform the first activation operation on the second feature map using the following formula:

$$p(F[c][j]) = \frac{e^{F[c][j]}}{\sum_{j=0}^{W \times H-1} e^{F[c][j]}}$$

wherein p represents an activation function, and F[c][j] represents the value of the j-th element in the second feature map of the c-th lead.

In some embodiments, the feature transformer 14 is further configured to perform the second activation operation on the embedded information using the following formula:

$$N(z) = - \sum_{j=0}^{W \times H - 1} p(F[c][j]) \log p(F[c][j])$$

wherein z represents a random variable of the c-th lead, and N represents the weight of the c-th lead.

In some embodiments, the feature transformer 14 is further configured to:

continuously input the feature weight of each lead to two fully connected layers to obtain an attention weight corresponding to each lead;

obtain the depth feature of each lead based on the attention weight corresponding to each lead and the first feature map.

In some embodiments, the feature extractor 13 is further configured to:

input the segmented waveform data of each lead into the trained ResNet14 model to obtain a first feature map corresponding to each lead, the first feature map corresponding to each lead being identical in size.

It should be understood that the units or modules recorded in the attention mechanism-based 12-lead ECG classification apparatus 10 correspond to the steps in the method described with reference to FIG. 2. Therefore, the operations and features described above for the method are also applicable to the attention mechanism-based 12-lead ECG classification apparatus 10. The attention mechanism-based 12-lead ECG classification apparatus 10 can be implemented in the browser of an electronic device or other secure applications in advance, or it can be loaded into the browser of an electronic device or other secure applications by downloading or the like. The respective units in the attention mechanism-based 12-lead ECG classification apparatus 10 may cooperate with the units in the electronic device to implement the solution of the embodiment of the present disclosure.

In summary, the attention mechanism-based 12-lead ECG classification apparatus proposed by the embodiment of the present disclosure effectively improves the accuracy of abnormality screening by performing feature extraction on the original image of the 12-lead ECG. Meanwhile, combined with the attention mechanism, it can give a higher degree of attention to the leads prone to ST-segment abnormalities, effectively improving the accuracy of abnormality screening.

For the several modules or units mentioned in the detailed description above, this division is not mandatory. In fact, according to the embodiment of the present disclosure, the features and functions of two or more modules or units described above may be embodied in one module or unit. Conversely, the features and functions of a module or unit described above may be further divided into multiple modules or units to be embodied.

Figure 9:
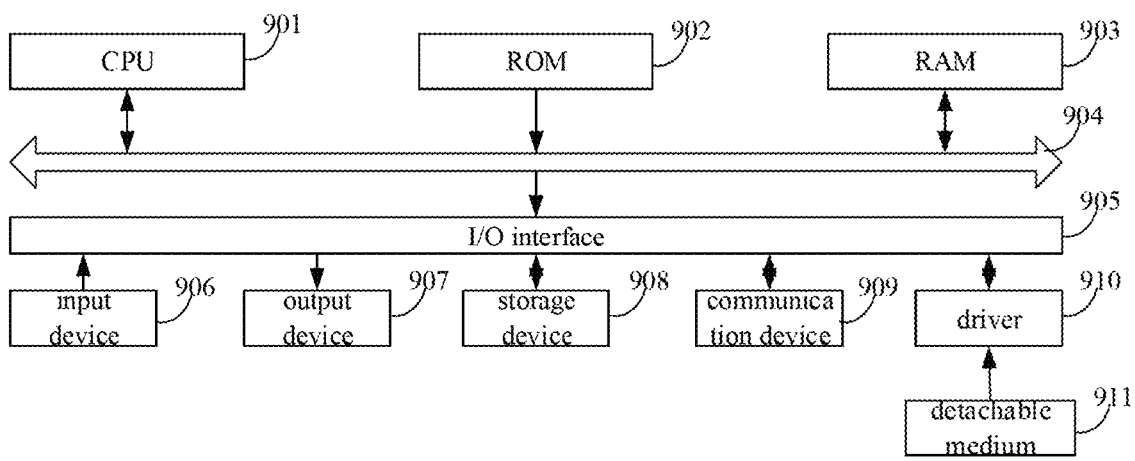
FIG. 9 is a schematic structural view of a computer system adapted to implement embodiments of the present disclosure.

Next, referring to FIG. 9, FIG. 9 illustrates a schematic structural view of a computer system adapted to implement the embodiments of the present disclosure.

As shown in FIG. 9, the computer system comprises a central processing unit (CPU) 901, which can perform various appropriate actions and processing according to computer instructions stored in a read-only memory (ROM) 902 or computer instructions loaded from a storage portion 908 to a random access memory (RAM) 903. Various computer instructions and data required for the operation instructions of the system are also stored in the RAM 903. The CPU 901, the ROM 902, and the RAM 903 are connected to each other through a bus 904. An input/output (I/O) interface 905 is also connected to the bus 904.

The following components are connected to the I/O interface 905: an input device 906 including a keyboard, a mouse, etc.; an output device 907 including a cathode ray tube (CRT), a liquid crystal display (LCD) and the like, and a loudspeaker and the like; a storage device 908 including a hard disk, etc.; and a communication device 909 including a network interface card such as a LAN card, a modem, and the like. The communication device 909 performs communication processing via a network such as the Internet. A driver 910 is also connected to the I/O interface 905 as needed. A detachable medium 911, such as a magnetic disk, an optical disk, a magneto-optical disk, a semiconductor memory, and the like, is installed on the driver 910 as needed, so that computer instructions read from therefrom can be installed into the storage device 908 as needed.

In particular, according to an embodiment of the present disclosure, the process described above with reference to the flow charts of FIG. 2 can be implemented as a computer software program. For example, an embodiment of the present disclosure comprises a computer program product, which includes computer instructions carried on a computer-readable medium. The computer instructions include program codes for executing the methods shown in the flow charts. In such an embodiment, the computer instructions include program code for executing the method shown in the flowchart. In such an embodiment, the computer instructions may be downloaded from the network by the communication device 909 and installed, and/or installed from the detachable medium 911. When the computer instructions are executed by the central processing unit (CPU) 901, the above-mentioned functions defined in the system of the present disclosure are performed.

It is to be noted that the computer-readable medium shown in the present disclosure may be a computer-readable signal medium or a computer-readable storage medium, or any combination thereof. The computer-readable storage medium may be, for example, but not limited to, an electrical, magnetic, optical, electromagnetic, infrared, or semiconductor system, apparatus or device, or any combination thereof. More specific examples of computer-readable storage media may include, but are not limited to: an electrical connection with one or more wires, a portable computer magnetic disk, a hard disk, a random access memory (RAM), a read-only memory (ROM), an erasable programmable read-only memory (EPROM or flash memory), an optical fiber, a portable compact disk read-only memory (CD-ROM), an optical storage device, a magnetic storage device, or any suitable combination thereof. In the present disclosure, the computer-readable storage medium may be any tangible medium that is contains or stores computer instructions, and the computer instructions may be used by or in combination with an instruction execution system, apparatus or device. In the present disclosure, the computer-readable signal medium may include a data signal propagated in a baseband or as a part of a carrier wave, and computer-readable program codes are carried therein. This propagated data signal may take various forms, including but not limited to an electromagnetic signal, an optical signal, or any suitable combination thereof. The computer-readable signal medium may also be any computer-readable medium other than the computer-readable storage medium.

The computer-readable medium may send, propagate or transmit computer instructions for use by or in combination with an instruction execution system, apparatus or device. The program codes contained on the computer-readable medium can be transmitted by any suitable medium, including but not limited to: wireless, wire, optical cable, RF, etc., or any suitable combination thereof.

The flow charts and block diagrams in the accompanying drawings illustrate the architectures, functions and operation instructions of possible implementations of the system, method and computer program product according to various embodiments of the present disclosure. In this regard, each block in the flow chart or block diagram may represent a module, a program segment or a part of a code, and the module, the program segment, or a part of the code contains one or more executable instructions for realizing specified logical functions. It is also to be noted that, in some alternative implementations, the functions marked in the blocks may also occur in a different order from the order marked in the drawings. For example, two consecutive blocks can actually be executed substantially in parallel, or they can sometimes be executed in a reverse order, depending on the functions involved. It is also to be noted that each block in the block diagram and/or flow chart, and a combination of is blocks in the block diagram and/or flow chart, can be implemented by a dedicated hardware-based system that performs specified functions or operation instructions, or can be implemented by a combination of dedicated hardware and computer instructions.

The units or modules involved in the embodiments of the present disclosure can be implemented in software or hardware. The described units or modules may also be provided in a processor, for example, it can be described as: a processor comprising an acquirer, a segmenter, a feature extractor, a feature transformer and a classifier. The names of these components do not constitute a limitation on the units or components themselves in certain cases.

As another aspect, the present disclosure further provides a non-transitory computer-readable storage medium. The computer-readable storage medium may be included in the electronic device described in the foregoing embodiments, and may also exist independently without being assembled into the electronic device. The aforementioned computer-readable storage medium stores one or more computer instructions, which is used to execute the attention mechanism-based 12-lead ECG classification method described in the present disclosure when the aforementioned computer instructions are executed by one or more processors.

What have been described are only the embodiments of the present disclosure and explanations of the applied technical principles. Those skilled in the art should understand that the inventive scope involved in the present disclosure is not limited to technical solutions formed by specific combinations of the above technical features, and should also encompass other technical solutions formed by any combinations of the above technical features or their equivalent features without departing from the inventive concept, for example, technical solutions formed by replacing the above features and technical features having similar functions as those disclosed in the is present disclosure (but not limited to) with each other.

The invention claimed is:

1. An attention mechanism-based 12-lead electrocardiogram classification method, comprising:
   acquiring an original image of a 12-lead electrocardiogram;
   segmenting waveform data recorded in the original image to obtain segmented waveform data for each lead in the 12-lead electrocardiogram;
   performing depth feature extraction on the segmented waveform data of said each lead to obtain a first feature map of each lead image of said each lead;
   performing feature transformation on the first feature map of said each lead based on an attention mechanism to obtain a depth feature of said each lead; and
   classifying the depth feature of said each lead to obtain a classification result for the original image;
   wherein said performing feature transformation on the first feature map of said each lead based on an attention mechanism to obtain a depth feature of said each lead comprises:
      performing at least one convolution operation processing on the first feature map to obtain a second feature map;
      performing a first activation operation on the second feature map to obtain embedded information;
      performing a second activation operation on the embedded information to obtain a feature weight corresponding to said each lead; and
      obtaining the depth feature of said each lead based on the feature weight and the first feature map.

2. The classification method according to claim 1, wherein said segmenting waveform data recorded in the original image to obtain segmented waveform data for said each lead in the 12-lead electrocardiogram comprises:
   for said each lead image, identifying a position of each target feature in the lead image; and
   for said each target feature, taking the position of the target feature as a center, and segmenting the waveform data based on a preset sliding window width to obtain segmented waveform data of each lead.

3. The classification method according to claim 1, wherein the first activation operation is performed on the second feature map using the following formula:

$$p(F[c][j]) = \frac{e^{F[c][j]}}{\sum_{j=0}^{W \times H - 1} e^{F[c][j]}}$$

wherein p represents an activation function, and F [c][j] represents a value of a j-th element in the second feature map of a c-th lead, where c and j are positive integers.

4. The classification method according to claim 1, wherein the second activation operation is performed on the embedded information using the following formula:

$$N(z) = - \sum_{j=0}^{W \times H - 1} p(F[c][j]) \log p(F[c][j])$$

wherein z represents a random variable of a c-th lead, and N represents a feature weight to which the c-th lead corresponds, where c and j are positive integers.

5. The classification method according to claim 1, wherein said obtaining the depth feature of said each lead based on the feature weight and the first feature map comprises:
   continuously inputting the feature weight of each lead into two fully connected layers to obtain an attention weight corresponding to each lead; and obtaining the depth feature of said each lead based on the attention weight corresponding to said each lead and the first feature map.

6. The classification method according to claim 5, wherein said continuously inputting the feature weight of each lead into two fully connected layers to obtain an attention weight corresponding to each lead comprises:
compressing a dimension of the feature weight of each lead using a first fully connected layer of the two fully connected layers to determine a dependency relationship between leads; and
calibrating the feature weight of each lead using the dependency relationship to obtain an attention weight corresponding to said each lead.

7. The classification method according to claim 5, wherein said obtaining the depth feature of each lead based on the attention weight corresponding to each lead and the first feature map comprises:
multiplying the first feature map of each lead by the attention weight corresponding to each lead to obtain the depth feature of each lead.

8. The classification method according to claim 1, wherein said performing depth feature extraction on the segmented waveform data of said each lead to obtain a first feature map of said each lead comprises:
inputting the segmented waveform data of said each lead into a trained neural network model to obtain the first feature map corresponding to each lead, the first feature map corresponding to said each lead being identical in size.

9. An electronic device comprising a memory and a processor, the memory storing computer instructions executable on the processor, wherein an attention mechanism-based 12-lead electrocardiogram classification method is implemented when the computer instructions are executed by the processor, the method comprising:
acquiring an original image of a 12-lead electrocardiogram;
segmenting waveform data recorded in the original image to obtain segmented waveform data for each lead in the 12-lead electrocardiogram;
performing depth feature extraction on the segmented waveform data of said each lead to obtain a first feature map of each lead image of said each lead;
performing feature transformation on the first feature map of said each lead based on an attention mechanism to obtain a depth feature of said each lead; and
classifying the depth feature of said each lead to obtain a classification result for the original image;
wherein said performing feature transformation on the first feature map of said each lead based on an attention mechanism to obtain a depth feature of said each lead comprises:
performing at least one convolution operation processing on the first feature map to obtain a second feature map;
performing a first activation operation on the second feature map to obtain embedded information;
performing a second activation operation on the embedded information to obtain a feature weight corresponding to said each lead; and
obtaining the depth feature of said each lead based on the feature weight and the first feature map.

10. A non-transitory computer-readable storage medium having computer instructions stored thereon, wherein an attention mechanism-based 12-lead electrocardiogram classification method is implemented when the computer instructions are executed by a processor, the method comprising:
acquiring an original image of a 12-lead electrocardiogram;
segmenting waveform data recorded in the original image to obtain segmented waveform data for each lead in the 12-lead electrocardiogram;
performing depth feature extraction on the segmented waveform data of said each lead to obtain a first feature map of each lead image of said each lead;
performing feature transformation on the first feature map of said each lead based on an attention mechanism to obtain a depth feature of said each lead; and
classifying the depth feature of said each lead to obtain a classification result for the original image;
wherein said performing feature transformation on the first feature map of said each lead based on an attention mechanism to obtain a depth feature of said each lead comprises:
performing at least one convolution operation processing on the first feature map to obtain a second feature map;
performing a first activation operation on the second feature map to obtain embedded information;
performing a second activation operation on the embedded information to obtain a feature weight corresponding to said each lead; and
obtaining the depth feature of said each lead based on the feature weight and the first feature map.

11. The non-transitory computer-readable storage medium according to claim 10, wherein said segmenting waveform data recorded in the original image to obtain segmented waveform data for said each lead in the 12-lead electrocardiogram comprises:
for said each lead image, identifying a position of each target feature in the lead image; and
for said each target feature, taking the position of the target feature as a center, and segmenting the waveform data based on a preset sliding window width to obtain segmented waveform data of each lead.

12. The non-transitory computer-readable storage medium according to claim 10, wherein the first activation operation is performed on the second feature map using the following formula:

$$p(F[c][j]) = \frac{e^{F[c][j]}}{\sum_{j=0}^{W \times H-1} e^{F[c][j]}}$$

wherein p represents an activation function, and F [c][j] represents a value of a j-th element in the second feature map of a c-th lead.

13. The non-transitory computer-readable storage medium according to claim 10, wherein the second activation operation is performed on the embedded information using the following formula:

$$N(z) = -\sum_{j=0}^{W \times H-1} p(F[c][j]) \log p(F[c][j])$$

where z represents a random variable of a c-th lead, and N represents a feature weight to which the c-th lead corresponds.

14. The non-transitory computer-readable storage medium according to claim 10, wherein said obtaining the depth feature of said each lead based on the feature weight and the first feature map comprises:
   continuously inputting the feature weight of each lead into two fully connected layers to obtain an attention weight corresponding to each lead; and
   obtaining the depth feature of said each lead based on the attention weight corresponding to said each lead and the first feature map.

15. The non-transitory computer-readable storage medium according to claim 14, wherein said continuously inputting the feature weight of each lead into two fully connected layers to obtain an attention weight corresponding to each lead comprises:
   compressing a dimension of the feature weight of each lead using a first fully connected layer of the two fully connected layers to determine a dependency relationship between leads; and
   calibrating the feature weight of each lead using the dependency relationship to obtain an attention weight corresponding to said each lead.

16. The non-transitory computer-readable storage medium according to claim 14, said obtaining the depth feature of each lead based on the attention weight corresponding to each lead and the first feature map comprises:
   multiplying the first feature map of each lead by the attention weight corresponding to each lead to obtain the depth feature of each lead.

17. The non-transitory computer-readable storage medium according to claim 10, wherein said performing depth feature extraction on the segmented waveform data of said each lead to obtain a first feature map of said each lead comprises:
   inputting the segmented waveform data of said each lead into a trained neural network model to obtain the first feature map corresponding to each lead, the first feature map corresponding to said each lead being identical in size.

18. The electronic device according to claim 9, wherein said segmenting waveform data recorded in the original image to obtain segmented waveform data for said each lead in the 12-lead electrocardiogram comprises:
   for said each lead image, identifying a position of each target feature in the lead image; and
   for said each target feature, taking the position of the target feature as a center, and segmenting the waveform data based on a preset sliding window width to obtain segmented waveform data of each lead.

* * * * *